United States Patent [19]

Kim et al.

[11] Patent Number: 5,158,950

[45] Date of Patent: * Oct. 27, 1992

[54] 1,3-DITHIOL-2-YLIDENE DERIVATIVES AND PROCESS FOR THE PREPARATION THEREOF

[75] Inventors: Choong S. Kim; Jeong S. Chae, both of Seoul; Young R. Choi, Kyonggi; Jong W. Lee, Kyounggi; Joung K. Yoo, Kyonggi, all of Rep. of Korea

[73] Assignee: Yuhan Corporation, Ltd., Seoul, Rep. of Korea

[*] Notice: The portion of the term of this patent subsequent to Apr. 7, 2009 has been disclaimed.

[21] Appl. No.: 527,521

[22] Filed: May 23, 1990

Related U.S. Application Data

[63] Continuation of Ser. No. 206,659, Jun. 15, 1988, abandoned.

[30] Foreign Application Priority Data

Jul. 1, 1987 [KR] Rep. of Korea .................. 87-6745

[51] Int. Cl.⁵ ............... C07D 409/12; C07D 339/06; A61K 31/385
[52] U.S. Cl. ........................... 514/231.5; 514/255; 514/269; 514/272; 514/363; 514/367; 514/370; 514/382; 514/397; 514/407; 514/422; 514/440; 544/145; 544/317; 544/331; 544/379; 544/405; 548/139; 548/163; 548/195; 548/246; 548/241; 548/527; 548/315.1; 548/365.7; 548/447; 549/39
[58] Field of Search ............... 549/39; 514/231.5, 255, 514/269, 272, 363, 367, 370, 382, 397, 407, 422, 440; 544/145, 317, 331, 379, 405; 548/139, 163, 195, 246, 241, 336, 374, 527

[56] References Cited

U.S. PATENT DOCUMENTS

| | | | |
|---|---|---|---|
| 4,327,223 | 4/1982 | Matsui et al. | 549/39 |
| 4,329,479 | 5/1982 | Yabutani et al. | 549/39 |
| 4,663,319 | 5/1987 | Iijima | 514/212 |
| 4,822,814 | 4/1989 | Ohyama | 514/440 |

FOREIGN PATENT DOCUMENTS

| | | |
|---|---|---|
| 85300187.3 | 7/1985 | European Pat. Off. |
| 85106746.2 | 2/1987 | European Pat. Off. |
| 2625012 | 12/1976 | Fed. Rep. of Germany |
| 49-101528 | 9/1974 | Japan |
| 54-63085 | 5/1979 | Japan |
| 55-33471 | 3/1980 | Japan |
| 59-42377 | 3/1984 | Japan |
| 60-215682 | 10/1985 | Japan |
| 61-275274 | 12/1986 | Japan |
| 62-158274 | 7/1987 | Japan |
| 8005842 | 10/1980 | Netherlands |

*Primary Examiner*—Robert Gerstl
*Attorney, Agent, or Firm*—Finnegan, Henderson, Farabow, Garrett and Dunner

[57] ABSTRACT 2-(1,3-Dithiol-2-ylidene)-2-[N-(substituted) carbamoly] acetate esters and salts thereof, having potent therapeutic or prophylactic effect for hepatic disorder, are provided. Processes for their preparation and intermediates in their preparation also are disclosed.

19 Claims, No Drawings

1,3-DITHIOL-2-YLIDENE DERIVATIVES AND PROCESS FOR THE PREPARATION THEREOF

This application is a continuation of Ser. No. 206,659, filed Jun. 15, 1988, now abandoned.

BACKGROUND OF THE INVENTION

1. Field of the Invention

The present invention relates to new 1,3-dithiol-2-ylidene derivatives and salts thereof which exhibit excellent therapeutic and prophylactic effect for hepatic diseases, production methods of these compounds and pharmaceutical compositions containing theses compounds at a dose suitable for daily administration.

2. Description of the Prior Art

Diisopropyl 2-(1,3-dithiol-2-ylidene)malonate (malotilate) is a known hepatoprotectant described, for example, by Y. Imaizu-mi, et. al.,(Jpn. J. Pharmacol. 1981, 31(1), 15-21).

This compound and many closely related compounds and the preparation thereof are disclosed in U.S. Pat. Nos. 4,329,479 and 4,327,223, Spain ES 536,228 Ger Offen 2,625,012, Jpn. Kokai Tokkyo Koho 54-63,085 and 55-33,471 and Neth. Appl. 8,005,842. Dithiol derivatives having a ketone functional group in the side chain are disclosed in Jpn. Kokai Tokkyo Koho 59-42,377, 60-215,682, 61-275,274, and 62-158,274 and Eur. Pa 210,284.

Other 1,3-dithiol-2-ylidene derivatives containing an amide functional groups in the side chain are disclosed in Eur. Pat. Appl. EP 149, 534.

SUMMARY OF THE INVENTION

In brief, the present invention relates to compounds of the general formula(I):

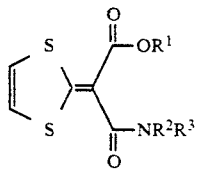

in which $R^1$ is a lower alkyl; $R^2$ is hydrogen or a lower alkyl; and $R^3$ is hydrogen, a lower alkyl, a cycloalkyl, aryl, tetrahydrothiophen-2-on-3-yl, 2-thiazolyl, 2-thiazolyl substituted by a lower alkyl at 4 and/or 5 position of the ring, 2-thiazolin-2-yl, 2-benzothiazolyl, 2-,3- or 4-pyridyl, 2-,3- or. 4-pyridyl substituted by halogen or a lower alkyl, pyrazinyl, 2-pyrimidyl, 2-hydroxy-4-pyrimidyl, 2-thienyl, 1,3,4-thiadiazol-2-yl, 1,3,4-thiadiazol-2-yl substituted by a lower alkyl or trifluoromethyl, 4-carboxamido-5-imidazolyl, 3-pyrazolyl, 5-methyl-3-isoxazolyl or 5-tetrazolyl; or R and R together with the nitrogen atom form a 5- or 6-membered (un)-saturated heterocyclic ring e.g. morpholine, thiomorpholine, piperidine, piperazine, N-alkylpiperazine, pyrrolidine, imidazole, pyrrole and proline, physiologically acceptable salts and hydrates thereof having less toxicity and improved pharmacological stability.

Accordingly, it is an object of the present invention to provide novel 1,3-dithiol-2-ylidene derivatives and salts thereof which possess excellent therapeutic and prophylactic effect for hepatic diseases.

Another object of the present invention is to provide production methods for said compounds.

A further object of the present invention is to provide pharmaceutical compositions containing said compounds at a dose suitable for daily administration.

DETAILED DESCRIPTION

The present invention provides compounds of the general formula (I),

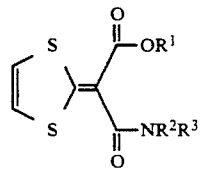

physiologically acceptable salts and hydrates thereof in which $R^1$ is a lower alkyl; $R^2$ is hydrogen or a lower alkyl; and $R^3$ is hydrogen, a lower alkyl, a cycloalkyl, aryl, tetrahydrothiophen-2-on-3-yl, 2-thiazolyl, 2-thiazolyl substituted by a lower alkyl at 4 and/or 5 position of the ring, 2-thiazolin-2-yl, 2-benzothiazolyl, 2-, 3- or 4-pyridyl, 2-, 3- or 4-pyridyl substituted 2-pyrimidyl, 2-hydroxy-4-pyrimidyl, 2-thienyl, 1,3,4-thiadiazol-2-yl, 1,3,4-thiadiazol-2-yl substituted by a lower alkyl or trifluoromethyl, 4-carboxamido-5-imidazolyl, 3-pyrazolyl, 5-methyl-3-isoxazolyl or 5-tetrazolyl; or $R^2$ and $R^3$ together with the nitrogen atom form a 5- or 6-membered (un)saturated heterocyclic ring e.g. morpholine, thiomorpholine, piperidine, piperazine, N-alkylpiperazine, pyrrolidine, imidazole, pyrrole and proline.

As used herein the term "lower alkyl" means a straight or branched chain $C_2$–$C_6$ alkyl. The term "cycloalkyl" means a cycloalkyl having a 3 to 6 membered ring (e.g. cyclopropyl, cyclobutyl, cyclopentyl, cyclohexyl and the like). The term "aryl" means phenyl optionally substituted by one or more radicals selected from the group consisting of $C_1$–$C_4$ alkyl, $C_1$–$C_6$ alkoxy, $C_1$–$C_4$ acyloxy, $C_1$–$C_4$ acylamido, hydroxy, carboxy, amino, nitro, halogen, trifluoromethyl and $C_1$–$C_4$ alkoxy carbonyl.

In a preferred class of compounds according to the invention the following groups have the meanings indicated;

$R^1$ is methyl, ethyl, isopropyl, sec-butyl or tert-butyl; $R^2$ and $R^3$ together with nitrogen atom form a morpholine, piperazine, N-methylpiperazine, pyrrolidine, imidazole or pyrrole ring.

In a particulary preferred class of compounds according to the invention the following groups have the meanings indicated;

$R^1$ is methyl, ethyl, isopropyl or sec-butyl; $R^2$ and $R^3$ independently are hydrogen, alkyl or cycloalkyl.

In another preferred class of compounds according to the invention the following groups have the meanings indicated;

$R^1$ is methyl, ethyl, isopropyl or sec-butyl; $R^2$ is hydrogen or methyl; $R^3$ is aryl or heterocyclic ring as defined above.

The compounds according to the invention can be administered orally or parenterally. They will in general be associated with a pharmaceutically acceptable carrier or diluent to provide a pharmaceutical composition. For oral administration the pharmaceutical composition can most conveniently be in the form of capsules or tablets, which may be slow releasing formulations. The composition may also take the form of a dragee or may be in syrup form.

A convenient daily dose by the oral route would be of the order of 100 mg to 1.0 g per day, in the form of dosage units containing from 50 to 200 mg per dosage unit.

Parenteral administration may be by injection at intervals or as a continuous infusion.

The compounds of the present invention may be made from an acid anhydride of the formula(II);

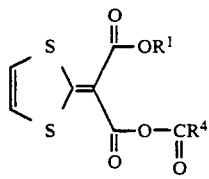

in which $R^1$ has the meanings given herein and $R^4$ is sec- or tert-butyl, lower alkoxy or benzyloxy by reacting a compound of formula(III);

HNR²R³    (III)

wherein $R^2$ and $R^3$ are the same as defined above.

The reaction may be carried out by allowing the acid anhydride and amine of the formula(III) to stand in a solvent such as methylene chloride, acetonitrile or alcohol. The reaction with weakly basic heterocyclic amines (e.g. 2-aminopyridine, 3-aminoisoxazole, 3-aminotriazole, aminopyrazine, 2-aminopyrimidine and 2-amino-1,3,4-thiadiazole) or aniline derivatives substituted with an electron withdrawing group (e.g. nitro, halogen, trifluoromethyl and carbonyl) on the benzene ring can be carried out by heating the reactants at 50°-100° C. in a solvent such as acetonitrile or dimethylformamide.

In an alternative procedure, the compounds of the present invention can be prepared from an active ester of formula(IV);

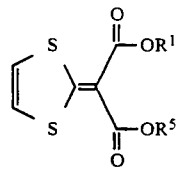

wherein $R^1$ is the same as defined above and $R^5$ is 1-benzotriazolyl, N-succinimidoyl, N-phthalimidoyl or arylsulfonyl, by reacting the amines of the formula(III).

The reaction can be carried out in a solvent (e.g. acetonitrile, methylene chloride and dimethylformamide) at 10°-100° C. The reaction with alkylamines or saturated heterocyclic amines (e.g. morpholine, thiomorpholine, piperidine, piperazine, pyrrolidine and the like) readily takes place at low temperature (10°-30° C.) while the reaction with weakly basic aryl or heterocyclic amines requires an elevated temperature (50°-100° C.).

In another process, the compound of the formula(I) can be prepared from a reaction mixture of monoacid of formula(V);

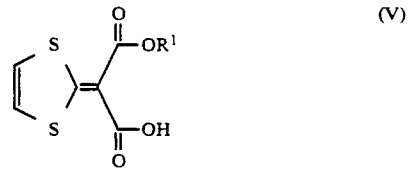

wherein $R^1$ is the same as defined above, and phosphorus pentachloride, by reacting the amines of the formula(III) in the presence of pyridine or triethyl amine since the acid chloride of the monoacid(V) cannot be isolated in a stable form. This reaction may be effected in a solvent (e.g. methylene chloride and acetonitrile) at a temperature from 0° C. to −15° C.

In another process, the products of the present invention can be prepared by reacting the compounds of formula(VI) and (VII);

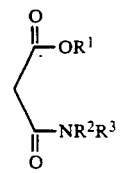

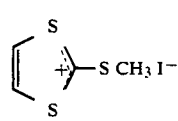

wherein $R^1$, $R^2$ and $R^3$ are the same as defined above, in a solvent such as tetrahydrofuran.

In another alternative process, the compound of formula(I) can be prepared from a starting material of formula(VIII);

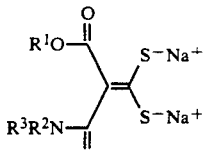

wherein $R^1$, $R^2$ and $R^3$ are the same as defined above. The above compounds of the formula(VIII) which can be generated in situ. or isolated under certain reaction conditions by reacting carbon disulfide and the compound of formula(VI) in the presence of sodium hydroxide. The above compounds(VIII) may be reacted with cis-1,2-dichloroethylene, 1,1-dichloroethylene, 1,1,1-trichloroethane or 1,1,2-trichloroethane. The reaction is preferably carried out at 15°-50° C. in an organic solvent, e.g. dimethylformamide.

In the above discussion of the processes available for the production of the compounds according to the invention references have been made to the acid anhydride of formula(II) and the active ester of formula(IV). These compounds are novel compounds and the invention includes such compounds. These intermediates may be made by processes described below.

Acid anhydrides of formula(II) may be prepared from the monoacid of formula(V) by reaction with the acid chloride of $R^5COOH$ wherein $R^5$ is the same as defined above in the presence of an organic base, e.g.

triethylamine or pyridine at 0°-30° C. The acid anhydrides of formula(II) used in this invention are isolated in a stable form.

The active ester of formula(IV) can be prepared by reacting the monoacid of formula(V) and 1-hydroxybenzotriazole, N-hydroxysuccinimide or N-hydroxyphthalimide in the presence of a dehydrating agent such as N,N'-dicyclo-hexylcarbodiimide. When R5 is an arylsulfonyl group, the active ester of formula(IV) may be prepared from the reaction of the monoacid of formula(V) with the corresponding arylsulfonyl chloride in the presence of an organic amine e.g. triethylamine and pyridine at 0°-30° C.

The monoacid of formula(V) can be prepared by hydrolyzing one ester group of formula(IX);

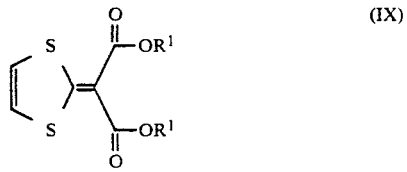

(IX)

wherein $R^1$ is the same as defined above, in the corresponding alcohol at ambient temperature or at refluxing temperature when $R^1$ is methyl.

The compound of formula(VII) can be prepared by the similar method described in the literature [J.C.S. Chem. Comm., 920 (1976)].

The starting material, the compound of formula(VI) may be prepared by simply reacting alkyl malonyl chloride with the corresponding amino compounds of formula(III).

In order that the invention may be more fully understood, the following Experiments and Examples are given by way of illustration only. Experiments describe protective and therapeutic effects of the compounds of formula(I) against hepatic damage. Examples exemplify the preparation of the compounds of formula(I), starting materials and related intermediates.

EXAMPLE 1

Monomethyl 2-(1,3-dithiol-2-ylidene)malonate

Dimethyl 2-(1,3-dithiol-2-ylidene)malonate (23.2 g) was added to a solution of potassium hydroxide (13.2 g) in methanol (500 m(). The mixture was refluxed for 5 hrs. The mixture was concentrated to dryness, the residue was dissolved in water (1l) and the insoluble material was removed by filtration. The filtrate was acidified to pH=4 with dil-HCl. The solid formed was filtered and recrystallized from methylene chloride to obtain the pure product (19.62 g, 90%).

| m.p.: | 180° C. |
|---|---|
| IR(KBr): | 1700 cm$^{-1}$ |
| NMR(DMSO-d$_3$)δ: | 3.87(s, 3H), 7.68(s, 2H) |

EXAMPLE 2

Monoethyl 2-(1,3-dithiol-2-ylidene) malonate

Diethyl 2-(1,3-dithiol-2-ylidene)malonate (26.0 g) was added to a solution of potassium hydroxide (13.2 g) in ethanol (700 ml). The mixture was stirred at room temperature for 72 hrs. The resultant solid was filtered and dissolved in water (1{). The aqueous solution was acidified to pH=4 with dil-HCl and the solid formed was filtered. The filtered solid was recrystallized from acetone to obtain the pure product (22 g, 94.8%)

| m.p.: | 178° C. |
|---|---|
| IR(KBr): | 1686 cm$^{-1}$ |
| NMR(CDCl$_3$)δ: | 1.42(t, 3H), 4.45(q, 2H), 7.62(s, 2H) |

EXAMPLE 3

Monoisopropyl 2-(1,3-dithiol-2-ylidene)malonate

Diisopropyl 2-(1,3-dithiol-2-ylidene)malonate (28.8 g) was added to a solution of potassium hydroxide (13.2 g) in isopropanol (600 ml) and the mixture was stirred at room temperature for 24 hrs. The solid formed was filtered, washed with isopropanol and then dissolved in water (1 l). The aqueous solution was acidified to pH=4 with dil-HCl and the resultant solid was filtered. Recrystallization of the solid filtered from methylene chloride gave the pure product. (23.8 g, 92.8%)

| m.p.: | 162° C. |
|---|---|
| IR(KBr): | 3400, 1690, 1670 cm$^{-1}$ |
| NMR(CDCl$_3$)δ: | 1.45(d, 6H), 5.30(m, 1H), 7.32(s, 2H) |

EXAMPLE 4

Mono-sec-butyl 2-(1,3-dithiol-2-ylidene)malonate

Di-sec-butyl 2-(1,3-dithiol-2-ylidene)malonate (31.6 g) was added to a solution of potassium hydroxide (6.6 g) in sec-butanol (800 ml). The mixture was stirred at room temperature for 24 hrs. The reaction mixture was poured into water (4l) and the insoluble material was removed by filtration. The filtrate was acidified to pH=4 with dil-HCl and the solid formed was filtered. The solid filtered was recrystallized from methylene chloride to give the pure product. (19.5 g, 75%)

| m.p.: | 128° C. |
|---|---|
| IR(KBr): | 1678 cm$^{-1}$ |
| NMR(CDCl$_3$)δ: | 1.00(t, 3H), 1.46(d, 3H), 1.76(m, 2H), 5.20(m, 1H), 7.32(s, 2H), 13.26(s, 1H) |

EXAMPLE 5 a) Isopropyl 2-(1,3-dithiol-2-ylidene)-2-(ethoxycarbonyloxycarbonyl)acetate

To a solution of monoisopropyl 2-(1,3-dithiol-2-ylidene) malonate (15 g), in methylene chloride (150 ml), was added triethylamine (9.2 ml). The mixture was cooled to 0° C., thereto was added dropwise ethyl chloroformate (6.84 g) and then stirred at the same temperature for an hour. The reaction mixture was washed with water and evaporated to dryness. The residue thus obtained was recrystallized from n-hexane to obtain the pure product. (19 g, 98%)

| m.p.: | 69.2° C. |
|---|---|
| IR(KBr): | 1761, 1635 cm$^{-1}$ |
| NMR(CDCl$_3$)δ: | 1.34(d, 6H), 1.44(t, 3H), 4.31(q, 2H), 5.20(m, 1H), 7.80(s, 2H) |

Similarly prepared were;

b) Methyl
2-(1,3-dithiol-2-ylidene)-2-(ethoxycarbonyloxycarbonyl)acetate

| | |
|---|---|
| yield: | 97.5% |
| m.p.: | 86.6° C. |
| IR(KBr): | 1778, 1640 cm$^{-1}$ |
| NMR(CDCl$_3$)δ: | 1.40(t, 3H), 3.90(s, 2H), 4.25(q, 2H) 7.43(s, 2H) | c) Ethyl
2-(1,3-dithiol-2-ylidene)-2-(ethoxycarbonyloxycarbonyl)acetate

| | |
|---|---|
| yield: | 98.3% |
| m.p.: | 68° C. |
| IR(KBr): | 1772 cm$^{-1}$ |
| NMR(CDCl$_3$)δ: | 1.35(t, 3H), 1.36(t, 3H), 4.30(q, 4H), 7.38(s, 2H) | d) sec-Butyl
2-(1,3-dithiol-2-ylidene)-2-(ethoxycarbonyloxycarbonyl)acetate

| | |
|---|---|
| yield: | 89.4% |
| m.p.: | 44° C. |
| IR(KBr)δ: | 1752, 1642 cm$^{-1}$ |
| NMR(CDCl$_3$)δ: | 0.97(t, 3H), 1.33(d, 3H), 1.38(t, 3H), 1.65(m, 2H), 4.33(q, 2H), 5.06(m, 1H), 7.38(s, 2H) |

EXAMPLE 6 a) Isopropyl
2-(1,3-dithiol-2-ylidene)-2-(pivaloyloxycarbonyl)acetate

Triethylamine (6.94 ml) was added to a solution of monoisopropyl 2-(1,3-dithiol-2-ylidene)malonate (10 g) in methylene chloride (100 ml). The mixture was cooled to 0° C. and thereto was added dropwise pivaloyl chloride (5.54 ml). The mixture was stirred for an hour. The reaction mixture was washed with water and dried. Removal of solvent followed by recrystallization of the residue from n-hexane afforded the pure product. (12 g, 91%)

| | |
|---|---|
| m.p.: | 76° C. |
| IR(KBr): | 1783, 1625 cm$^{-1}$ |
| NMR(CDCl$_3$)δ: | 1.33(s, 9H), 1.37(d, 6H), 5.21(m, 1H), 7.43(s, 2H) |

In a similar manner was prepared from monomethyl 2-(1,3-dithiol-2-ylidene)malonate and pivaloyl chloride;

b) Methyl
2-(1,3-dithiol-2-ylidene)-2-(pivaloyloxycarbonyl)acetate

| | |
|---|---|
| yield: | 93.2% |
| m.p.: | 73° C. |
| IR(KBr): | 1741, 1637 cm$^{-1}$ |
| NMR(CDCl$_3$)δ: | 1.34(s, 9H), 3.88(s, 3H), 7.41(s, 2H) |

EXAMPLE 7 a) Isopropyl
2-(1,3-dithiol-2ylidene)-2-(1-benzotriazolyloxycarbonyl)acetate

A mixture of monoisopropyl 2-(1,3-dithiol-2-ylidene)malonate (9.84 g), 1-hydroxybenzotriazole (5.40 g), N,N'-dicyclohexylcarbodiimide (9.07 g) and methylene chloride (100 ml) was stirred at room temperature for 24 hrs. The solid formed was filtered. The filtrate was washed with water and evaporated to dryness. The residue thus obtained was treated with ethyl ether to give the titled compound. (12.4 g), 85.2%)

| | |
|---|---|
| m.p.: | 135° C. |
| IR(KBr): | 1679, 1653 cm$^{-1}$ |
| NMR(CDCl$_3$)δ: | 1.44(d, 6H), 5.30(m, 1H), 7.35(s, 2H) 7.20–7.60(m, 3H), 8.10(m, 1H) |

Similarly prepared was;

b) sec-Butyl
2-(1,3-dithiol-2-ylidene)-2-(1-benzotriazolyloxycarbonyl)acetate

| | |
|---|---|
| yield: | 89.4% |
| m.p.: | 123° C. |
| IR(KBr): | 1701, 1654 cm$^{-1}$ |
| NMR(CDCl$_3$)δ: | 0.99(t, 3H), 1.39(d, 3H), 1.68(q, 2H), 5.16(m, 1H), 7.34(s, 2H), 7.45(m, 3H), 8.05(m, 1H) |

EXAMPLE 8

Isopropyl
2-(1,3-dithiol-2-ylidene)-2-(N-succinimidoyloxycarbonyl)acetate

Monoisopropyl 2-(1,3-dithiol-2-ylidene)-malonate(10.0 g) and N-hydroxysuccinimide (4.72 g) were dissolved in methylene chloride (100 ml) and thereto was added N, N'-dicyclohexyl-carbodiimide (8.67 g). The mixture was stirred at room temperature for 24 hrs. The solid formed was removed by filtration and the filtrate was washed with water. After removal of solvent the resultant residue was recrystallized from ether to afford a white crystalline product. (8.0 g, 57.1%)

| | |
|---|---|
| m.p.: | 212° C. |
| IR(KBr): | 1726.4, 1683, 1647.6 cm$^{-1}$ |
| NMR(CDCl$_3$)δ: | 1.35(d, 6H), 2.9(s, 4H), 5.3(m, 1H), 7.3(s, 2H) |

EXAMPLE 9

Isopropyl 2-(1,3-dithiol-2-ylidene)-2-carbamoylacetate

Isopropyl 2-(1,3-dithiol-2-ylidene)-2-(ethoxycarbonyloxy-carbonyl)acetate (20.65 g) was added to a solution of ammonia in acetonitrile (150 ml) and the mixture was stirred at room temperature for an hour. The reaction mixture was evaporated to dryness and the residue was recrystallized from methylene chloride to obtain the pure product. (12.0 g, 77%)

| | |
|---|---|
| m.p.: | 77.5° C. |

-continued

| IR(KBr): | 1650 cm$^{-1}$ |
|---|---|
| NMR(CDCl$_3$)δ: | 1.45(d, 6H), 5.30(m, 1H), 7.40(s, 2H) |

EXAMPLE 10

Isopropyl 2-(1,3-dithiol-2-ylidene)-2-(N-methylcarbamoyl)acetate

To a solution of isopropyl 2-(1,3-dithiol-2-ylidene)-2-(ethoxycarbonyloxycarbonyl)acetate (6.36 g) in acetonitrile (50 ml), was added dropwise methylamine (40% aqueous solution) (3.44 ml) and stirred at room temperature for an hour. The mixture was evaporated to dryness and the residue was recrystallized from a mixture of methylene chloride and n-hexane to give the titled compound. (4.66 g, 95%)

| m.p.: | 114.7° C. |
|---|---|
| IR(KBr): | 3320, 1678 cm$^{-1}$ |
| NMR(CDCl$_3$)δ: | 1.42(d, 6H), 2.92(d, 3H), 5.27(m, 1H) 7.10(s, 2H) |

EXAMPLE 11

Isopropyl 2-(1,3-dithiol-2-ylidene)-2-(N-isopropylcarbamoyl)acetate

A mixture of isopropyl 2-(1,3-dithiol-2-ylidene)-2-(pivaloyloxycarbonyl)acetate (13.2g), isopropylamine (2.6 g) and methylene chloride (60 ml) was stirred at room temperature for 5 hrs. The reaction mixture was washed with aqueous sodium hydroxide solution and water. After removal of solvent the residue was distilled to give the titled compound (9.43 g, 66%) as a yellow oil.

| b.p.: | 172° C. (5 mmHg) |
|---|---|
| IR(neat): | 1660 cm$^{-1}$ |
| NMR(DMSO-d$_6$)δ: | 1.17(d, 6H), 1.35(d, 6H), 3.92(m, 1H), 5.10(m, 1H), 7.49(s, 2H) |

EXAMPLE 12

Isopropyl 2-(1,3-dithiol-2-ylidene)-2-(N-cyclohexylcarbamoyl)acetate

A solution of isoproyl 2-(1,3-dithiol-2-ylidene)-2-(pivaloyloxycarbonyl)acetate (13.2 g) and cyclohexylamine (3.97 g) in methylene chloride (100ml) was stirred at room temperature for 2 hrs. The reaction mixture was washed with aqueous sodium hydroxide solution and water and then evaporated to dryness. The resultant residue was recrystallized from ethyl acetate to afford the pure product. (12.0 g, 91.6%)

| m.p.: | 97.8° C. |
|---|---|
| IR(KBr): | 3400, 1645, 1600 cm$^{-1}$ |
| NMR(CDCl$_3$)δ: | 1.00-2.30(m, 10H), 1.45(d, 6H), 3.90(m, 1H), 5.30(m, 1H), 7.08(s, 2H) |

EXAMPLE 13

Isopropyl 2-(1,3-dithiol-2-ylidene)-2-(N,N-diethylcarbamoyl)acetate

Isopropyl 2-(1,3-dithiol-2-ylidene)-2-(ethoxycarbonyloxy-carbonyl)acetate (13.7 g) and diethylamine (3.66 g) were dissolved in methylene chloride (100 ml). The mixture was stirred at room temperature for 2 hrs. The reaction mixture was washed with dil-HCl, aqueous sodium hydroxide solution and then water. After removal of solvent the residue was distilled under vacuum to obtain the titled compound (9.0 g, 66%) as a pale yellow oil.

| IR(neat): | 1600, 1620 cm$^{-1}$ |
|---|---|
| NMR(CDCl$_3$)δ: | 1.22(t, 6H), 1.28(d, 6H), 3.44(q, 4H), 5.11(m, 1H), 6.74(dd, 2H) |

EXAMPLE 14 a) Isopropyl 2-(1,3-dithiol-2-ylidene)-2-8 N-(tetrahydrothiophen-2-on-3-yl)carbamoyl]acetate Homocysteine thiolactone hydrochloride (4.8 g) was dissolved in ethanol (100 ml) and thereto was added triethylamine (8 ml). To the mixture was added isopropyl 2-(1,3-dithiol-2-ylidene)-2-ethoxycarbonyloxycarbonyl)acetate (10 g). The mixture was stirred at room temperature for an hour. The solid formed was filtered and recrystallized from ethyl acetate to give the titled compound. (9.5 g, 89%)

| m.p.: | 129° C. |
|---|---|
| IR(KBr): | 3300, 1680, 1610 cm$^{-1}$ |
| NMR(CDCl$_3$)δ: | 1.45(d, 6H), 2.00-3.50(m, 4H), 4.60(m, 1H), 5.30(m, 1H), 7.15(s, 2H), 9.05(d, 1H) |

In a similar manner was prepared b) Ethyl 2-(1,3-dithiol-2-ylidene)-2-[N-(tetrahydrothiophen-2-on-3-yl)carbamoyl]acetate

| yield: | 85.0% |
|---|---|
| m.p.: | 145° C. |
| IR(KBr): | 3281, 1693, 1648, 1604 cm$^{-1}$ |
| NMR(CDCl$_3$)δ: | 1.50(t, 3H), 1.80-3.60(m, 4H), 4.43(q, 2H), 4.63(m, 1H), 7.15(s, 2H) |

EXAMPLE 15

Isopropyl 2-(1,3-dithiol-2-ylidene)-2-[(2-carboxypyrrolidin-1-yl)carbonyl]acetate Isopropyl 2-(1,3-dithiol-2-ylidene)-2-(ethoxycarbonyloxy-carbonyl)acetate (13.2 g) and proline (4.6 g) was dissolved in DMF (60 ml). The mixture was stirred at room temperature for 24 hrs, thereto was added conc-HCl (20 ml) and stirred for a further 2 hrs. The reaction mixture was poured into ice water and basified to pH=12 with aqueous sodium hydroxide solution. The mixture was washed with methylene chloride and the aqueous layer was acidified to pH=2 with dil-HCl. The solid formed was filtered and recrystallized from ethyl acetate and n-hexane to obtain the pure product (12.5 g, 91%).

| | |
|---|---|
| m.p.: | 167.8° C. |
| IR(KBr): | 1720, 1660 cm$^{-1}$ |
| NMR(CDCl$_3$)δ: | 1.29(d, 6H), 2.20(m, 4H), 3.53(m, 2H), 4.50(m, 1H), 5.10(m, 1H), 7.10(s, 2H) |

EXAMPLE 16

Isopropyl 2-(1,3-dithiol-2-ylidene)-2-(N-methyl-N-phenylcarbamoyl)acetate

Isopropyl 2-(1,3-dithiol-2-ylidene)-2-(ethoxycarbonyloxy-carbonyl)acetate (15.9 g) and N-methylaniline (6.43 g) were dissolved in methylene chloride (100 ml). The solution was stirred at room temperature for 24 hrs. The resultant mixture was washed with aqueous sodium hydroxide solution, dil-HCl and water. After removal of solvent the residue was purified by column chromatography on silica gel using petroleum ether-/ethyl acetate (9:1) as an eluent to give the product (13.2 g, 78.7%) as a yellow oil.

| | |
|---|---|
| IR(neat): | 1658, 1632 cm$^{-1}$ |
| NMR(CDCl$_3$)δ: | 1.16(d, 6H), 3.52(s, 3H), 4.89(m, 1H), 6.74(s, 2H), 7.20(m, 5H) |

EXAMPLE 17 a) Isopropyl 2-(1,3-dithiol-2-ylidene)-2-(N-phenylcarbamoyl)acetate

Isopropyl 2-(1,3-dithiol-2-ylidene)-2-(ethoxycarbonyloxy-carbonyl)acetate (12.72 g) and aniline (3.73 g) were dissolved in methylene chloride (100 ml). The mixture was stirred at room temperature for 24 hrs. The reaction mixture was washed with aqueous sodium hydroxide solution, dil-HCl and then water. The methylene chloride layer was dried and the solvent was distilled. The resultant residue was recrystallized from ethyl acetate to obtain the pure product. (11.3 g, 88.0%)

| | |
|---|---|
| m.p.: | 86.6° C. |
| IR(KBr): | 3350, 1664 cm$^{-1}$ |
| NMR(CDCl$_3$)δ: | 1.46(d, 6H), 5.30(m, 1H), 7.13(s, 2H), 7.00-7.86(m, 5H) |

Similarly prepared were b) sec-Butyl 2-(1,3-dithiol-2-ylidene)-2-(N-phenylcarbamoyl)acetate

| | |
|---|---|
| yield: | 86.5% |
| m.p.: | 60-62° C. |
| IR(KBr): | 3358, 1662, 1624 cm$^{-1}$ |
| NMR(CDCl$_3$)δ: | 1.0(t, 3H), 1.4(d, 3H), 1.8(q, 2H), 5.2(m, 1H), 7.2(s, 2H), 7.1-7.7(m, 5H), 10.9(bs, 1H) | c) Ethyl 2-(1,3-dithiol-2-ylidene)-2-(N-phenylcarbamoyl)acetate

| | |
|---|---|
| yield: | 84.2% |
| m.p.: | 97.6° C. |
| IR(KBr): | 3350, 1665, 1620 cm$^{-1}$ |
| NMR(CDCl$_3$)δ: | 1.50(t, 3H), 4.46(q, 2H), 7.20(s, 2H), 7.00-8.00(m, 5H), 10.80(bs, 1H) | d) Methyl 2-(1,3-dithiol-2-ylidene)-2-(N-phenylcarbamoyl)acetate

| | |
|---|---|
| yield: | 73.6% |
| m.p.: | 92.5° C. |
| IR(KBr): | 1670, 1620 cm$^{-1}$ |
| NMR(CDCl$_3$)δ: | 3.98(s, 3H), 7.15(s, 2H), 7.05-7.70(m, 5H), 10.70(bs, 1H) | e) Isopropyl 2-(1,3-dithiol-2-ylidene)-2-[N-(4-methylphenyl)carbamoyl]acetate

| | |
|---|---|
| yield: | 98.0% |
| m.p.: | 143° C. |
| IR(KBr): | 3460, 1660 cm$^{-1}$ |
| NMR(CDCl$_3$)δ: | 1.49(d, 6H), 2.32(s, 3H), 5.31(m, 1H), 7.10 & 7.50(dd, 4H), 7.15(s, 2H) | f) Isopropyl 2-(1,3-dithiol-2-ylidene)-2-[N-(2,3-dimethylphenyl)carbamoyl]acetate

| | |
|---|---|
| yield: | 81.0% |
| m.p.: | 139° C. |
| IR(KBr): | 3400, 1660, 1610, 1540 cm$^{-1}$ |
| NMR(CDCl$_3$)δ: | 1.48(d, 6H), 2.26(s, 3H), 2.33(s, 3H), 5.38(m, 1H), 7.14(s, 2H), 6.98-8.08(m, 3H) | g) Isopropyl 2-(1,3-dithiol-2-ylidene)-2-[N-(4-chlorophenyl)carbamoyl]acetate

| | |
|---|---|
| yield: | 80.1% |
| m.p.: | 173° C. |
| IR(KBr): | 3350, 1660 cm$^{-1}$ |
| NMR(CDCl$_3$)δ: | 1.48(d, 6H), 5.33(m, 1H), 7.18(s, 2H), 7.30 & 7.56(dd, 4H) | h) Isopropyl 2-(1,3-dithiol-2-ylidene)-2-[N-(3-chlorophenyl)carbamoyl]acetate

| | |
|---|---|
| yield: | 54% |
| m.p.: | 121-121.5° C. |
| IR(KBr): | 3350, 1670, 1600 cm$^{-1}$ |
| NMR(CDCl$_3$)δ: | 1.48(d, 6H), 5.33(m, 1H), 7.18(s, 2H), 7.83-6.95(m, 4H) | i) Isopropyl 2-(1,3-dithiol-2-ylidene)-2-[N-(4-fluorophenyl)carbamoyl]acetate

| | |
|---|---|
| yield: | 80.1% |
| m.p.: | 173-173.2° C. |
| IR(KBr): | 3350, 1660, 1612 cm$^{-1}$ |
| NMR(CDCl$_3$)δ: | 1.47(d, 6H), 5.33(m, 1H), 7.18(s, 2H), |

7.18–7.69(m, 4H), 11(s, 1H)

j) Isopropyl 2-(1,3-dithiol-2-ylidene)-2-[N-(2-fluorophenyl)carbamoyl]acetate

| | |
|---|---|
| yield: | 73.4% |
| m.p.: | 135.6–135.7° C. |
| IR(KBr): | 3360, 1660, 1612 cm$^{-1}$ |
| NMR(CDCl$_3$)δ: | 1.5(d, 6H), 5.4(m, 1H), 7.2(s, 2H), 7–8.7(m, 4H), 10.9(s, 1H) | k) Isopropyl 2-(1,3-dithiol-2-ylidene-2-[n-(3-chloro-4-fluoropheyny)carbamoyl]acetate

| | |
|---|---|
| yield: | 80.3% |
| m.p.: | 158.4–158.5° C. |
| IR(KBr): | 3350, 1660, 1620 cm$^{-1}$ |
| NMR(CDCl$_3$)δ: | 1.48(d, 6H), 5.32(m, 1H), 7.19(s, 2H), 7.05–7.99(m, 3H) | l) Isopropyl 2-(1,3-dithiol-2-ylidene)-2-[N-(4-methoxyphenyl)carbamoyl]acetate

| | |
|---|---|
| yield: | 79% |
| m.p.: | 124.4–124.9° C. |
| IR(KBr): | 3220, 1670, 1590 cm$^{-1}$ |
| NMR(CDCl$_3$)δ: | 1.4(d, 6H), 3.8(s, 3H), 5.3(m, 1H), 7.2(s, 2H), 6.8 & 7.5(dd, 4H), 10.7(s, 1H) | m) Ethyl 2-(1,3-dithiol-2-ylidene)-2-[N-(4-methoxyphenyl)carbamoyl]acetate

| | |
|---|---|
| yield: | 90.8% |
| m.p.: | 132–134° C. |
| IR(KBr): | 3216, 1664, 1607 cm$^{-1}$ |
| NMR(CDCl$_3$)δ: | 1.47(t, 3H), 3.8(s, 3H), 4.46(2H, q), 7.1(s, 2H), 6.7–7.7(m, 4H), 10.6(bs, 1H) | n) sec-Butyl 2-(1,3-dithiol-2-ylidene)-2-[N-(4-methoxyphenyl)carbamoyl]acetate

| | |
|---|---|
| yield: | 93.5% |
| m.p.: | 76° C. |
| IR(KBr): | 3088, 1665, 1593 cm$^{-1}$ |
| NMR(CDCl$_3$)δ: | 1.15(t, 3H), 1.51(d, 3H), 1.82(q, 2H), 3.84(s, 3H), 5.24(m, 1H), 7.02(s, 2H), 6.8–7.6(m, 4H), 10.8(s, 1H) | o) isopropyl 2-(1,3-dithiol-2-ylidene)-2-[N-(3-methoxyphenyl)carbamoyl]acetate

| | |
|---|---|
| yield: | 79.3% |
| m.p.: | 101.1° C. |
| IR(KBr)δ: | 1670, 1590 cm$^{-1}$ |
| NMR(CDCl$_3$)δ: | 1.54(d, 6H), 3.85(s, 3H), 5.35(m, 1H), 6.74(m, 1H), 7.21(s, 2H), 7.32(m, 3H) | p) Isopropyl 2-(1,3-dithiol-2-ylidene)-2-[N-(3-nitrophenyl)carbamoyl]acetate

| | |
|---|---|
| yield: | 35.5% |
| m.p.: | 194–194.8° C. |
| IR(KBr): | 3400, 1660, 1620 cm$^{-1}$ |
| NMR(CDCl$_3$)δ: | 1.50(d, 6H), 5.33(m, 1H), 7.21(s, 2H), 7.2–8.58(m, 4H) | q) Isopropyl 2-(1,3-dithiol-2-ylidene)-2-[N-(4-acetamidophenyl)carbamoyl]acetate

| | |
|---|---|
| yield: | 85% |
| m.p.: | 207.5–209° C. |
| IR(KBr): | 3260, 1670, 1610 cm$^{-1}$ |
| NMR(CDCl$_3$)δ: | 1.5(d, 6H), 2.15(s, 3H), 5.4(m, 1H), 7.2(s, 2H), 7.5(d, 4H) | r) Isopropyl 2-(1,3-dithiol-2-ylidene)-2-[N-(3-acetamidophenyl)carbamoyl]acetate

| | |
|---|---|
| yield: | 82.5% |
| m.p.: | 199.5° C. |
| IR(KBr): | 3390, 1670, 1610, 1600 cm$^{-1}$ |
| NMR(CDCl$_3$)δ: | 1.50(d, 6H), 2.15(s, 3H), 5.35(m, 1H), 7.32(m, 6H), 7.80(s, 1H) | s) Isopropyl 2-(1,3-dithiol-2-ylidene)-2-[N-(4-trifluoromethylphenyl)carbamoyl]acetate

| | |
|---|---|
| yield: | 36% |
| m.p.: | 131° C. |
| IR(KBr): | 1676, 1626 cm$^{-1}$ |
| NMR(CDCl$_3$)δ: | 1.5(d, 6H), 5.35(m, 1H), 7.2(s, 2H), 7.5–7.9(dd, 4H) | t) Isopropyl 2-(1,3-dithiol-2-ylidene)-2-[N-(3-trifluoromethylphenyl)carbamoyl]acetate

| | |
|---|---|
| yield: | 82% |
| m.p.: | 129° C. |
| IR(KBr): | 1667, 1595 cm$^{-1}$ |
| NMR(CDCl$_3$)δ: | 1.5(d, 6H), 5.33(m, 1H), 7.20(s, 2H), 7.3–8.0(m, 4H) |

EXAMPLE 18 a) Isopropyl 2-(1,3-dithiol-2-ylidene)-2-[N-(2-pyridyl)carbamoyl]acetate

Isopropyl 2-(1,3-dithiol-2-ylidene)-2-(1-benzotriazolyloxy-carbonyl) acetate (7.26 g) and 2-aminopyridine (2.11 g) were dissolved in dimethylformamide (50 ml). The mixture was stirred at 70° C. for 24 hrs. The mixture was poured into ice-water and extracted with methylene chloride. The combined extracts were washed with aqueous sodium hydroxide solution and water. After removal of solvent the residue obtained was recrystallized from ethyl acetate to give the pure product. (4.6 g, 71%)

| | |
|---|---|
| m.p.: | 135° C. |
| IR(KBr): | 1657, 1618 cm$^{-1}$ |
| NMR(CDCl$_3$)δ: | 1.50(d, 6H), 5.31(m, 1H), 7.00(m, 1H), 7.19(s, 2H), 7.70(m, 1H), 8.26(m, 2H) |

The compound obtained above was treated with HCl-ether to give the corresponding hydrochloride as pale yellow crystals.

| | |
|---|---|
| m.p.: | 164–166° C. |
| IR(KBr): | 1633, 1601 cm$^{-1}$ |
| NMR(CDCl$_3$)δ: | 1.54(d, 6H), 5.42(m, 1H), 7.40(m, 3H), 8.40(m, 3H), 12.3(bs, 1H) |

Similarly prepared were b) sec-Butyl 2-(1,3-dithiol-2-ylidene)-2-[N-(2-pyridyl) carbamoyl]acetate

| | |
|---|---|
| yield: | 54.7% |
| m.p.: | 98° C. |
| IR(KBr): | 3434, 1661, 1620 cm$^{-1}$ |
| NMR(CDCl$_3$)δ: | 1.00(t, 3H), 1.48(d, 3H), 1.86(m, 2H), 5.22(m, 1H), 7.06(m, 1H), 7.20(s, 2H), 7.66(m, 1H), 8.26(m, 2H), 10.24(bs, 1H) | c) Isopropyl 2-(b 1,3-dithiol-2-ylidene)-2-[N-(3-pyridyl) carbamoyl]acetate

| | |
|---|---|
| yield: | 83% |
| m.p.: | 149° C. |
| IR(KBr): | 1665.8, 1615 cm$^{-1}$ |
| NMR(CDCl$_3$)δ: | 1.5(d, 6H), 5.3(m, 1H), 7.2(s, 2H), 7.2(m, 1H), 8.2–8.8(m, 3H), 11.1(s, 1H) | d) Isopropyl 2-(1,3-dithiol-2-ylidene)-2-[N-(4-pyridyl) carbamoyl]acetate

| | |
|---|---|
| yield: | 80.4% |
| m.p.: | 191.5° C. |
| IR(KBr): | 1660, 1623 cm$^{-1}$ |
| NMR(CDCl$_3$)δ: | 1.54(d, 6H), 5.36(m, 1H), 7.24(s, 2H), 7.58(d, 2H), 8.46(d, 2H), 11.26(bs, 1H) | e) Isopropyl 2-(1,3-dithiol-2-ylidene)-2-[N-(4-methyl-2-pyridyl) carbamoyl]acetate

| | |
|---|---|
| yield: | 18% |
| m.p.: | 144–145° C. |
| IR(KBr): | 3200, 1662( 1622 cm$^{-1}$ |
| NMR(CDCl$_3$)δ: | 1.45(d, 6H), 2.34(s, 3H), 5.36(m, 1H), 6.81(m, 1H), 7.20(m, 2H), 8.18(m, 2H), 11.19(bs, 1H) | f) Isopropyl 2-(1,3-dithiol-2-ylidene)-2-[N-(6-methyl-2-pyridyl) carbamoyl]acetate

| | |
|---|---|
| yield: | 53.5% |
| m.p.: | 158–160° C. |
| IR(KBr): | 3214, 1660, 1619 cm$^{-1}$ |
| NMR(CDCl$_3$)δ: | 1.58(d, 6H), 2.42(s, 3H), 5.32(m, 1H), 6.85(d, 1H), 7.18(s, 2H), 7.59(t, 1H), 8.10(d, 1H), 11.1(s, 1H) | g) Isopropyl 2-(1,3-dithiol-2-ylidene)-2-[N-(5-chloro-2-pyridyl)carbamoyl]acetate

| | |
|---|---|
| yield: | 45% |
| m.p.: | 177–178° C. |
| IR(KBr): | 1661.3, 1621.6 cm$^{-1}$ |
| NMR(CDCl$_3$)δ: | 1.5(d, 6H), 5.3 (m, 1H), 7.2(s, 2H), 7.4–7.6(m, 1H), 8.2 & 8.4(dd, 2H) | h) Isopropyl 2-(1,3-dithiol-2-ylidene)-2-[N-(5-methyl-3-isoxazolyl) carbamoyl]acetate

| | |
|---|---|
| yield: | 82.3% |
| m.p.: | 171° C. |
| IR(KBr): | 1664, 1607 cm$^{-1}$ |
| NMR(CDCl$_3$)δ: | 1.56(d, 6H), 2.41(s, 3H), 5.43(m, 1H), 6.79(s, 1H), 7.23(s, 2H), 11.18(bs, 1H) | i) Isopropyl 2-(1,3-dithiol-2-ylidene)-2-[N-(1,3,4-thiadiazol-2-yl) carbamoyl]acetate

| | |
|---|---|
| yield: | 60% |
| m.p.: | 185° C. |
| IR(KBr): | 1665, 1618.8 cm$^{-1}$ |
| NMR(CDCl$_3$)δ: | 1.5(d, 6H), 5.4(m, 1H), 7.35(s, 2H), 8.80(s, 1H), 12.3(bs, 1H) | j) Isopropyl 2-(1,3-dithiazol-2-ylidene)-2-[N-(5-methyl-1,3,4-thiadiazol-2-yl) carbamoyl]acetate

| | |
|---|---|
| yield: | 47.6% |
| m.p.: | 223° C. |
| IR(KBr): | 1653, 1615 cm$^{-1}$ |
| NMR(CDCl$_3$)δ: | 1.52(d, 6H), 2.74(s, 3H), 5.40(m, 1H), 7.36(s, 2H), 12.14(bs, 1H) | k) Isopropyl 2-(1,3-dithiol-2-ylidene)-2-[N-(5-trifluoromethyl-1,3,4-thiadiazol-2-yl) carbamoyl]acetate

| | |
|---|---|
| yield: | 31% |
| m.p.: | 182° C. |
| IR(KBr): | 1666, 1623 cm$^{-1}$ |
| NMR(DMSO-d$_5$)δ: | 1.51(d, 6H), 5.43(m, 1H), 7.73(s, 2H), 12.80(bs, 1H) | l) Isopropyl 2-(1,3-dithiol-2-ylidene)-2-[N-(pyrazin-2yl) carbamoyl]acetate

| yield: | 30% |
|---|---|
| m.p.: | 180-182°C. |
| IR(KBr): | 1664.5, 1626.0 cm$^{-1}$ |
| NMR(CDCl$_3$)δ: | 1.5(d, 6H), 5.3(m, 1H), 7.2(s, 2H), 8.3(s, 2H), 9.6(s, 1H), 11.3(bs, 1H) | m) Isopropyl 2-(1,3-dithiol-2-ylidene-2-[N-(2-hydroxy-4-pyrimidy) carbamoyl]acetate

| yield: | 67% |
|---|---|
| m.p.: | 300° C. |
| IR(KBr): | 3346, 1660, 1625 cm$^{-1}$ |
| NMR(CF$_3$COOD+CDCl$_3$)δ: | 1.6(d, 6H), 5.5(m, 1H), 6.7(d, 1H), 7.8(s, 2H), 8.3(d, 1H) | n) Isopropyl 2-(1,3-dithiol-2-ylidene)-2-[N-(2-benzothiazolyl) carbamoyl]acetate

| yield: | 33.0% |
|---|---|
| m.p.: | 235° C. |
| IR(KBr): | 1660, 1613 cm$^{-1}$ |
| NMR(CDCl$_3$+DMSO-d$_3$)δ: | 1.50(d, 6H), 5.42(m, 1H), 7.30-8.00(m, 4H), 7.61(s, 2H), 12.40(bs, 1H) | o) Isopropy 2-(1,3-dithiol-2-ylidene)-2-[N-(4-carboxamido-5-imidazolyl) carbamoyl]acetate

| yield: | 45.8% |
|---|---|
| m.p.: | 236° C. |
| IR(KBr): | 3326, 3119, 1665, 1586 cm$^{-1}$ |
| NMR(DMSO-d$_3$)δ: | 1.48(d, 6H), 5.36(m, 1H), 7.12(bs, 2H), 7.31(s, 1H), 7.68(s, 2H), 11.86(bs, 1H), 12.64(bs, 1H) |

EXAMPLE 19 a) Isopropyl 2-(b 1,3-dithiol-2-ylidene)-2-[N-(2-thiazolyl)-carbamoyl) acetate

Isopropyl 2-(1,3-dithiol-2-ylidene)-2-(ethoxycarbonyloxy-carbaony) acetate (12.74 g) and 2-aminothiazole (4.4 g) were dissolved in methylene chloride (150 ml). The mixture was stirred at room temperature for 72 hrs. The resultant solid was removed by filtration and the filtrate was washed with aqueous sodium hydroxide solution and water. After evaporation the residue was recyrsallized from ethyl acetate to give the titled compound (4.20 g), 32%).

| m.p.: | 156° C. |
|---|---|
| IR(KBr): | 3350, 1655, 1604 cm$^{-1}$ |
| NMR(CDCl$_3$)δ: | 1.49(d, 6H), 5.34(m, 1H), 6.25(d, 1H), 7.25(s, 2H), 7.48(d, 1H), 10.92(bs, 1H) |

The compound obtained above was treated with HCl-ehter to give the corresponding hydrochloride as a pale yellow crystal.

| m.p.: | 199-201° C. |
|---|---|
| IR(KBr): | 3397, 1670, 1627 cm$^{-1}$ |
| NMR(DMSO-d$_6$)δ: | 1.42(d, 6H), 5.20(m, 1H), 7.30(d, 1H), 7.56(d, 1H), 7.80(s, 2H) |

Similarly prepared were b) Ethyl 2-(1,3-dithiol-2-ylidene)-2-[N-2-thiazolyl)-carbamoyl-]acetate

| yield: | 34.5% |
|---|---|
| m.p.: | 142° C. |
| IR(KBr): | 3336, 1663, 1605 cm$^{-1}$ |
| NMR(CDCl$_3$)δ: | 1.52(t, 3H), 4.50(q, 2H), 6.95(d, 1H), 7.30(s, 2H), 7.50(d, 1H) | c) sec-Butyl 2-(1,3-dithiol-2-ylidene)-2-[N-(2-thiazolyl)-carbamoyl-]acetate

| yield: | 28.4% |
|---|---|
| m.p.: | 124° C. |
| IR(KBr): | 3185, 1657, 1612 cm$^{-1}$ |
| NMR(CDCl$_3$)δ: | 1.00(t, 3H), 1.41(d, 3H), 1.83(q, 2H), 5.22(m, 1H), 7.21(s, 2H), 6.96 & 7.51(dd, 2H), 12.04(bs, 1H) | d) Isopropyl 2-(1,3-dithiol-2-ylidene)-2-[N-(4-methyl-2-thiazolyl) carbamoyl]acetate

| yield: | 45.6% |
|---|---|
| m.p.: | 158° C. |
| IR(KBr): | 3348, 1653, 1605 cm$^{-1}$ |
| NMR(CDCl$_3$)δ: | 1.50(d, 6H), 2.35(d, 3H), 5.35(m, 1H), 6.49(q, 1H), 7.25(s, 2H) | e) Isopropyl 2-(1,3-dithiol-2-ylidene)-2-[N-(5-methyl-2-thiazolyl) carbamoyl]acetate

| yield: | 27.7% |
|---|---|
| m.p.: | 209° C. |
| IR(KBr): | 1655, 1616 cm$^{-1}$ |
| NMR(CDCl$_3$)δ: | 1.50(d, 6H), 2.40(d, 3H), 5.35(m, 1H), 7.10(q, 1H), 7.25(s, 2H) | f) Isopropyl 2-(1,3-dithiol-2-ylidene)-2-[N-(4,5-dimethyl-2-thiazolyl) carbamoyl]acetate

| yield: | 54% |
|---|---|
| m.p.: | 125.5° C. |
| IR(KBr): | 1653, 1612 cm$^{-1}$ |
| NMR(CDCl$_3$)δ: | 1.50(d, 6H), 2.30(s, 6H), 5.30(m, 1H), 7.21(s, 2H), 11.82(bs, 1H) | g) Isopropyl 2-(1,3-dithiol-2-ylidene)-2-[N-(2-thienyl)-carbamoyl]acetate

| | |
|---|---|
| yield: | 50.4% |
| m.p.: | 143° C. |
| IR(KBr): | 3164, 1631, 1543 cm$^{-1}$ |
| NMR(CDCl$_3$)δ: | 1.45(d, 6H), 5.32(m, 1H), 6.73(m, 3H), 7.16(s, 2H), 11.60(bs, 1H) |

EXAMPLE 20 a) Isopropyl 2-(1,3-dithiol-2-ylidene)-2-[N-(3-pyrazolyl)-carbamoyl]acetate

Isopropyl 2-(1,3-dithiol-2-ylidene)-2-(1-benzotriazolyloxy-carbonyl) acetate (25.5 g) and 3-aminopyrazole (6.3 g) were dissolved in acetonitrile (40 ml). The solution was stirred at room temperature for 15 hrs. The solid formed was filtered and recyrstallized from methylene chloride to give the pure product. (8.55 g), 40%)

| | |
|---|---|
| m.p.: | 174° C. |
| IR(KBr): | 3354, 1653, 1618 cm$^{-1}$ |
| NMR(DMSO-d$_3$)δ: | 1.45(d, 6H), 5.30(m, 1H), 6.60 & 7.15(dd, 2H), 7.15(s, 2H), 10.90(s, 1H) |

Similarly prepared was b) Isopropyl 2-(1,3-dithiol-2-ylidene)-2-[N-(5-tetrazolyl)-carbamoyl]acetate

| | |
|---|---|
| yield: | 81% |
| m.p.: | 258° C. |
| IR(KBr): | 1663, 1636 cm$^{-1}$ |
| NMR(DMSO-d$_3$)δ: | 1.40(d, 6H), 5.20(m, 1H), 7.80(s, 2H), 11.8(s, 1H) |

EXAMPLE 21 a) Ethyl 2-(1,3-dithiol-2-ylidene)-2-(n-cyclohexylcarbamoyl) acetate

Ethyl 2-cyclohexylcarbamoyl)acetat (2.15 g) was dissolved in THF (50 ml) and thereto was added portionwise sodium hydride (60% dispersion in oil) (0.48 g). To the mixture was added 2-methylthio-1,3-dithiolium iodide (2.77 g) and stirred at room temperature for an hour. The reaction mixture was poured into ice-water. The solid formed was filtered and recrystallized from ethyl acetate to obtain the pure product. (2.58 g, 81.9%)

| | |
|---|---|
| m.p.: | 91° C. |
| IR(KBr): | 3394, 1653, 1596 cm$^{-1}$ |
| NMR(CDCl$_3$)δ: | 1.45(t, 3H), 1.10-2.20(m, 10H), 3.90(m, 1H), 4.39(q, 2H), 7.09(s, 2H) |

Similiarly prepared was b) Ethyl 2-(1,3-dithiol-2-ylidene)-2-[N-(4-methyl-2-thiazolyl) carbamoyl]acetate

| | |
|---|---|
| yield: | 56.1% |
| m.p.: | 175° C. |
| IR(KBr): | 3321, 1659, 1625 cm$^{-1}$ |
| NMR(CDCl$_3$)δ: | 1.50(t, 3H), 2.37(s, 3H), 4.50(q, 2H), 6.48(s, 1H), 7.26(s, 2H) | c) Ethyl 2-(1,3-dithiol-2-ylidene)-2-(N-phenylcarbamoyl)-acetate

| | |
|---|---|
| yield: | 62.8% | d) Isopropyl 2-1,3-dithiol-2-ylidene)-2-(N-pyrimidin-2-ylcarbamoyl) acetate

| | |
|---|---|
| yield: | 37.5% |
| m.p.: | 135° C. |
| IR(KBr): | 3356.5, 1656.6, 1618.2 cm$^{-1}$ |
| NMR(CDCl$_3$)δ: | 1.5(d, 6H), 5.35(m, 1H), 7.2(s, 2H), 6.9-8.3(m, 4H) |

EXAMPLE 22 a) Isopropyl 2-(1,3-dithiol-2-ylidene)-2-[N-(4-hydroxyphenyl) carbamoyl]acetate Isopropyl 2-(1,3-dithiol-2-ylidene)-2-(ethoxycarbaonyloxy-carbonyl) acetate (13.2 g) and p-aminophenol (4.8 g) were dissolved in methylene chloride (100 ml). The mixture was stirred at room temperature for 20 hrs. To the reaction mixture was added conc-HCl (2 ml) and stirred for 1 hr. The resultant mixture was washed with water and then dried. The solution was evaporated and the residue was recrystallized from ethy acetate to obtain the pure product. (13 g, 97%)

| | |
|---|---|
| m.p.: | 85.5° C. |
| IR(KBr): | 1645 cm$^{-1}$ |
| NMR(CDCl$_3$)δ: | 1.50(d, 6H), 5.35(m, 1H), 6.49(s, 1H), 6.78 & 7.32(dd, 4H), 7.14(s, 2H) |

In a similar manner were prepared b) Ethyl 2-(1,3-dithiol-2-ylidene)-2-[N-(4-hydroxyphenyl)-carbamoyl]acetate

| | |
|---|---|
| yield: | 87.4% |
| m.p.: | 174° C. |
| IR(KBr): | 3213, 1657, 1604 cm$^{-1}$ |
| NMR(CDCl$_3$)δ: | 1.40(t, 3H), 4.40(q, 2H), 6.76 & 7.40(dd, 4H), 7.60(s, 2H), 9.20(s, 1H), 10.20(bs, 1H) | c) Isopropyl 2-(1,3-dithiol-2-ylidene)-2-[N-(3-hydroxyphenyl)carbamoyl]acetate

| | |
|---|---|
| yield: | 65% |
| m.p.: | 183.7° C. |
| IR(KBr): | 3250, 1664, 1603 cm$^{-1}$ |
| NMR(CDCl$_3$)δ: | 1.50(d, 6H), 5.40(m, 1H), 7.10(m, 4H), 7.20(s, 2H), 9.20(s, 1H), 11.10(bs, 1H) | d) Isopropyl 2-(1,3-dithiol-2-ylidene)-2-[N-(2-hydroxyphenyl)carbamoyl]acetate

| | |
|---|---|
| yield: | 71.1% |
| m.p.: | 184° C. |
| IR(KBr): | 3310, 3140, 1658, 1610 cm$^{-1}$ |
| NMR(CDCl$_3$)δ: | 1.48(d, 6H), 5.40(m, 1H), 7.05(m, 4H), 7.22(s, 2H), 9.15(s, 1H) | e) Isopropyl 2-(1,3-dithiol-2-ylidene)-2-[N-(2-thiazolin-2-yl)carbamoyl]acetate

| | |
|---|---|
| yield: | 25.5% |
| m.p.: | 165° C. |
| IR(KBr): | 1670, 1620 cm$^{-1}$ |
| NMR(CDCl$_3$)δ: | 1.48(d, 2H), 3.28(t, 2H), 4.04(t, 2H), 5.34(m, 1H), 7.27(s, 2H), 11.3(bs, 1H) |

EXAMPLE 23 a) Isopropyl 2-(1,3-dithiol-2-ylidene)-2-(N-cyclohexylcarbamoyl)acetate

To a solution of monoisopropyl 2-(1,3-dithiol-2-ylidene) malonate (4.92 g) in methylene chloride (50 ml), was added portionwise phosphorous pentachlroide (4.16 g) at −10° c. and stirred for an hour. To the mixture was added triethylamine (7 ml) and then cyclohexylamine (1,7 g). The mixture was stirred for an hour and poured into ice-water. The solid formed was filtered and recrystallized from ethyl acetate to give the titled compound. (4.56 g), 69.7%)

In a similar manner was prepared b) Isopropyl 2-(1,3-dithiol-2-ylidene)-2-(N-phenylcarbamoyl) acetate

| | |
|---|---|
| yield: | 59.4% |

EXAMPLE 24 a) Isopropyl 2-(1,3-dithiol-2-ylidene)-2-[N-(4-acetoxyphenyl)carbamoyl]acetate Isopropyl 2-(1,3-dithiol-2-ylidene)-2-[N-(4-hydroxyphenyl) carbamoyl]acetate (13.5 g) and triethylamine (6.7 ml) were dissolved in methylene chloride (100 ml) and cooled to 0° C. To the mixture was added acetyl chloride (3.16 ml) dropwise and then stirred for 1 hr. The reaction mixture was washed with water and dried over anhydrous magnesium sulfate. The solution was evaporated to dryness and the residue was triturated with n-hexane to give the titled compound. (12 g), 79.1%)

| | |
|---|---|
| m.p.: | 130.8° C. |
| IR(KBr): | 1750, 1660, 1610 cm$^{-1}$ |
| NMR(CDCl$_3$)δ: | 1.48(d, 6H), 2.27(s, 3H), 5.35(m, 1H), 7.05(d, 2H), 7.15(s, 2H), 7.60(d, 2H) |

Similarly prepared were b) Isopropyl 2-(1,3-dithiol-2-ylidene)-2-[N-(3-acetoxyphenyl)carbamoyl]acetate

| | |
|---|---|
| yield: | 93.9% |
| m.p.: | 130.9° C. |
| IR(KBr): | 1745, 1672, 1590 cm$^{-1}$ |
| NMR(CDCl$_3$)δ: | 1.49(d, 6H), 2.45(s, 2H), 5.35(m, 1H), 7.15(m, 5H), 8.5(m, 1H) | c) Isopropyl 2-(1,3-dithiol-2ylidene)-2-[N-(2-acetoxyphenyl)carbamoyl]acetate

| | |
|---|---|
| yield: | 93.9% |
| m.p.: | 130.8° C. |
| IR(KBr): | 3400, 1750, 1655, 1620 cm$^{-1}$ |
| NMR(CDCl$_3$)δ: | 1.48(d, 6H), 2.45(s, 3H), 5.33(m, 1H), 7.13(s, 2H), 7.10-8.60(m, 4H), 11.50(s, 1H) |

EXAMPLE 25 a) Isopropyl 2-(1,3-dithiol-2-ylidene)-2-[N-(2-carboxyphenyl)carbamoyl]acetate Isopropyl 2-(1,3-dithiol-2-ylidene)-2-(ethoxycarbonyloxy-carbonyl)acetate (15.9 g) and anthranilic acid (14 dissolved in DMF (100 ml). The mixture was stirred at 60° C. for hrs. The reaction mixture was poured into ice-water. The solid formed was filtered and recrystallized from ethyl acetate to give the titled compound. (5.6 g, 30.7%)

| | |
|---|---|
| m.p.: | 193° C. |
| IR(KBr): | 1670, 1660, 1620 cm$^{-1}$ |
| NMR(DMSO-d$_3$)δ: | 1.46(d, 6H), 5.26(m, 1H), 7.6(s, 2H), 7.8(m, 4H), 11.92(s, 1H) |

In a similar manner was prepared b) Isopropyl 2-(1,3-dithiol-2-ylidene)-2-N-(2-methoxycarbonylphenyl)carbamoyl]acetate

| | |
|---|---|
| yield: | 71.2% |
| m.p.: | 113.8° C. |
| IR(KBr): | 3200, 1700, 1660 cm$^{-1}$ |
| NMR(CDCl$_3$)δ: | 1.47(d, 6H), 3.93(s, 2H), 5.43(m, 1H), 7.15(s, 2H), 6.80-8.63(m, 4H), 12.16(s, 1H) |

EXAMPLE 26 a) Isopropyl 2-(1,3-dithiol-2-ylidene)-2-(4-morpholinylcarbonyl)acetate

Isopropyl 2-(1,3-dithiol-2-ylidene)-2-(ethoxycarbonyloxy-carbonyl]acetate (20 g) and morpholine (6.23 acetonitrile (200 ml). The mixture was stirred at room temperature for 2 hrs. The reaction mixture was evaporated to dryness and the residue was dissolved inmethylene chloride (100 ml). The solution was washed with aqueous sodium hydroxide solution and water. After evaporation the residue was recyrstallized from ethyl acetate and n-hexane to give the titled compound. (15.0 g, 71.1%)

| m.p.: | 123° C. |
|---|---|
| IR(KBr): | 1660, 1630 cm$^{-1}$ |
| NMR(CDCl$_3$)δ: | 1.30(d, 6H), 3.65(m, 8H), 5.20(m, 1H), 6.80(dd, 2H) |

Similarly prepared were b) Isopropyl 2-(1,3-dithiol-2-ylidene)-2-[(4-methylpiperazin-1-yl)carbonyl]acetate

| yield: | 64.1% |
|---|---|
| m.p.: | 82.5° C. |
| IR(KBr): | 1660, 1620 cm$^{-1}$ |
| NMR(CDCl$_3$)δ: | 1.30(d, 6H), 2.33(s, 3H), 2.40(m, 4H), 3.65(m, 4H), 5.18(m, 1H), 6.82(dd, 2H) | c) Isopropyl 2-(1,3-dithiol-2-ylidene)-2-(1-pryrrolidinylcarbaonyl)acetate

| yield: | 95.2% |
|---|---|
| m.p.: | 112° C. |
| IR(KBr): | 1660, 1610 cm$^{-1}$ |
| NMR(CDCl$_3$)δ: | 1.30(d, 6H), 1.95(m, 4H), 3.20-3.80(m, 4H), 5.16(m, 1H), 6.81(dd, 2H) | d) Isopropyl 2-(1,3-dithiol-2-ylidene)-2-(1-imidazolylcarbaony)acetate

| yield: | 45.3% |
|---|---|
| m.p.: | 178° C. |
| IR(KBr): | 1660, 1610 cm$^{-1}$ |
| NMR(CDCl$_3$)δ: | 1.14(d, 6H), 5.08(m, 1H), 7.07(s, 1H), 7.27(s, 2H), 7.35(s, 1H), 7.92(s, 1H) |

EXAMPLE 27

Isopropyl 2-(1,3-dithiol-2-ylidene)-2-(N-phenylcarbamoyl) acetate

Isopropyl N-phenylcarbamoylacetate (21.1 g) was dissolved in acetone (50 ml) and thereto was added carbon disulfide (6.1 ml). The solution was cooled to 020 C. To the mixture was added aqueous sodium hydroxide solution (8.4 g in 10 ml water). The mixture was stirred at the same temperature for an hour, and then cis-1,2-dichloroethylene (9.7 g) was added dropwise thereto. The mixture was stirred at 30° C. for 3 hrs. After cooling, the mixture was poured into ice-water. The solid formed was filtered and recrystallized from ethyl acetate to give the titled compound. (12.5 g, 40%)

EXPERIMENT 1

Protective effect against acute hepatic damage induced by carbon tetrachloride Principle; Carbon tetrachloride (CCl$_4$) is a well-known hepatotoxic agent, thus widely used to produce experimental animal models for screening the potential drugs acting upon hepatic diseases. In this experiment test compounds were administered to mice prior to treatment with CCl$_4$. 24 Hours after the CCl$_4$ treatment, the animals were sacrificed and serum alanine aminotransferase (ALT) levels were determined. The hepatoprotective effect of a test compound was evaluated by the suppressive action against the increase of serum ALT induced by CCl$_4$.

Method; The experimental animals were divided into normal, CCl$_4$ treated and test compound treated groups. Each group consisted of 8 mice with body weight of 20–25 grams. The test compounds were suspended in 0.2% sodium carboxy methyl cellulose (CMC-Na) solution and administered orally at the dose of 50 mg/125 ml/kg body weight. Only the vehicle, 0.2% CMC-Na solution, was administered to the normal and to the CCl$_4$ treated group instead of the test compound suspension. 6 Hours after the drug administration, the CCl$_4$ solution in olive oil was administered orally to the CCl$_4$ treated- and the test compound treated group at the dose of 50 ul/25 ml olive oil/kg body weight. The normal group was administered olive oil only at the same dose. 24 Hours after the CCl$_4$ administration, blood samples were collected from the orbital sinus of the animals and the sera were obtained by centrifugation The serum ALT activities were monitored using an automatic blood analyzer (Gilford, SBA 300). The hepatoprotective effect of the test compounds was expressed by the suppressive percentage against the increase of serum ALT level induced by CCl$_4$ calculated by the following formula;

Hepatoprotective effect (%) =

$$\frac{\text{ALT level(CCl}_4\text{ group)} - \text{ALT level (test group)}}{\text{ALT level(CCl}_4\text{ group)} - \text{ALT level (normal grp)}} \times 100$$

Results: The test results are shown in Table I.

TABLE I

Protective effect of test compound against increase of serum ALT activity induced by CCl$_4$

| Compound of Example No. | Inhibitory (%) |
|---|---|
| 9 | 65.5 |
| 10 | 92.0 |
| 11 | 49.4 |
| 12 | 98.0 |
| 13 | 55.6 |
| 14(a) | 99.2 |
| 14(b) | 88.7 |
| 15 | 14.0 |
| 16 | 47.9 |
| 17(a) | 100.1 |
| 17(b) | 99.8 |
| 17(c) | 100.1 |
| 17(d) | 98.2 |
| 17(e) | 100.5 |
| 17(f) | 92.0 |
| 17(g) | 81.5 |
| 17(h) | 97.5 |

TABLE I-continued

Protective effect of test compound against increase of serum ALT activity induced by $CCl_4$

| Compound of Example No. | Inhibitory (%) |
|---|---|
| 17(i) | 89.8 |
| 17(k) | 93.8 |
| 17(l) | 99.6 |
| 17(m) | 61.5 |
| 17(n) | 96.5 |
| 17(o) | 100.0 |
| 17(q) | 78.2 |
| 17(r) | 46.6 |
| 17(s) | 100.0 |
| 17(t) | 96.0 |
| 17(u) | 75.0 |
| 18(a) | 99.8 |
| 18(b) | 100.0 |
| 18(c) | 100.4 |
| 18(d) | 99.7 |
| 18(e) | 99.7 |
| 18(f) | 100.2 |
| 18(g) | 77.3 |
| 18(h) | 100.1 |
| 18(i) | 100.0 |
| 18(j) | 100.0 |
| 18(l) | 99.8 |
| 18(m) | 12.8 |
| 18(n) | 15.2 |
| 18(o) | 98.7 |
| 19(a) | 100.1 |
| 19(b) | 100.8 |
| 19(c) | 100.0 |
| 19(d) | 97.2 |
| 19(e) | 9.2 |
| 19(f) | 91.4 |
| 20(a) | 102.1 |
| 20(b) | 99.9 |
| 21(d) | 99.8 |
| 22(a) | 99.2 |
| 22(b) | 90.9 |
| 22(c) | 93.0 |
| 22(d) | 16.2 |
| 22(e) | 99.4 |
| 24(a) | 101.7 |
| 24(b) | 98.0 |
| 24(c) | 22.8 |
| 25(a) | 74.0 |
| 26(a) | 66.5 |
| 26(b) | 46.0 |
| 26(c) | 90.5 |
| 26(d) | 98.0 |

EXPERIMENT 2

Determination of 50% Inhibitory Dose ($ID_{50}$) of test Compounds

Principle The various doses of test compounds were administered to mice, followed by the treatment with $CCl_4$ after 6 hours. 24 Hours after the $CCl_4$ treatment, the serum ALT level of the animals were determined. The hepatoprotective effect of the test compounds and the doses were plotted to form dose-response curves. The $ID_{50}$ doses of the test compounds were estimated from the dose-response curves.

Method; The experimental animals were divided into normal, $CCl_4$ treated and test compound treated groups. Each group consisted of 8 mice with body weight of 20-25 grams. The test compounds were suspended in 0.2% CMC-Na solution and administered orally at a dose of 50 mg, 25 mg, 12.5 mg, or 6.25 mg/125 ml/kg body weight. Only the vehicle, 0.2% CMC-Na solution, was administered to the normal and to the $CCl_4$ treated group instead of the test compound suspension. 6 Hours after the drug administration, the $CCl_4$ solution in olive oil was administered orally to the $CCl_4$ treated and the test compound treated groups at the dose of 50 ul/25 ml olive oil/kg body weight. The normal group was administered olive oil only at the same dose. 24 Hours after the $CCl_4$ administration, blood samples were collected from the orbital sinus of the animals and the sera were obtained by centrifugation. The serum ALT activities were monitored and the hepatoprotective effect of the test compounds were calculated by the same method as described in experiment 1. The inhibitory percentages were plotted against the corresponding doses of the test compounds to make dose-response curves. The 50% inhibitory dose of test compound was estimated from the dose-response curve.

Results; The $ID_{50}$ doses of the test compounds were shown at the Table II.

TABLE II $ID_{50}$ of test compound

| Compound of Example No. | $ID_{50}$ (mg/kg) |
|---|---|
| 14(a) | 10.0 |
| 14(b) | 25.0 |
| 17(a) | 8.0 |
| 17(b) | 12.5 |
| 17(c) | 8.0 |
| 17(d) | 20.0 |
| 17(k) | 6.25 |
| 17(m) | 50.0 |
| 17(n) | 10.0 |
| 18(a) | <6.25 |
| 18(b) | 7.0 |
| 18(c) | 6.25 |
| 18(d) | <6.25 |
| 18(e) | 20.0 |
| 18(f) | 12.5 |
| 18(g) | 25.0 |
| 18(h) | 9.0 |
| 18(i) | <6.25 |
| 18(j) | 10.0 |
| 18(l) | <6.25 |
| 18(o) | 25.0 |
| 19(a) | 6.25 |
| 19(b) | 6.25 |
| 19(c) | <6.25 |
| 19(d) | <6.25 |
| 19(e) | 25.0 |
| 20(a) | 8.0 |
| 20(b) | 10.0 |
| 22(a) | 12.5 |
| 22(b) | <12.5 |

EXPERIMENT 3

Each test compound was suspended in a 0.2% CMC-Na solution in various concentrations to make test suspension. The test suspensions were administered orally to male ICR mice (10 in each group) at various doses. The number of dead mice was counted for 14 days and the value of mediam lethal dose ($LD_{50}$, g/kg) was calculated by the Hitchifield-Wilcoxon method.

The results are shown in Table III.

TABLE III $LD_{50}$ of Test Compound

| Compound of Example No. | $LD_{50}$ (g/kg) |
|---|---|
| 11 | 2.6 |
| 14(a) | >5 |
| 14(b) | >4 |
| 17(a) | 3.0 |
| 17(b) | >5 |
| 17(c) | >5 |
| 17(g) | >5 |
| 17(h) | >5 |
| 17(i) | >5 |

TABLE III-continued

| Compound of Example No. | LD$_{50}$ of Test Compound LD$_{50}$ (g/kg) |
|---|---|
| 17(j) | >5 |
| 17(l) | >5 |
| 17(n) | >5 |
| 17(q) | >5 |
| 17(s) | >4 |
| 18(a) | 4.2 |
| 18(b) | 5.0 |
| 18(d) | 1.1 |
| 18(e) | >5 |
| 18(f) | >5 |
| 18(g) | >5 |
| 18(h) | >5 |
| 18(i) | >5 |
| 18(j) | >5 |
| 18(l) | >5 |
| 18(m) | >5 |
| 18(n) | >5 |
| 18(o) | >5 |
| 19(a) | >5 |
| 19(b) | 2.5 |
| 19(d) | 5.0 |
| 19(f) | >5 |
| 20(a) | 5.0 |
| 20(b) | 5.0 |
| 21(d) | 3.2 |
| 22(a) | >5 |
| 22(c) | >5 |
| 22(e) | >5 |
| 24(b) | >5 |
| 25(a) | 1.2 |

What is claimed is:

1. A compound of the formula (I)

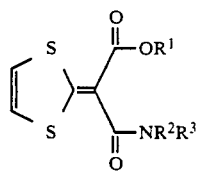

or a physiologically acceptable salt or hydrate thereof in which:

$R^1$ is a straight or branched alkyl group having 1 to 4 carbon atoms;

$R^2$ is hydrogen or a straight or branched alkyl group having 1 to 3 carbon atoms; and $R^3$ is a cyclohexyl; tetrahydrothiophen-2-on-3-yl; 2-thiazolyl; 2-thiazolyl substituented by a lower alkyl having 1 to 3 carbon atoms at the 4 and/or 5 position of the ring; 2-thiazolin-2-yl; 2-benzothiazolyl; pyrazinyl; 2-pyrimidyl; 2-hydroxy-4-pyrimidyl; 2-thienyl; 1,3,4-thiadiazol-2-yl; 1, 3, 4-thiadiazol-2-yl s alkyl having 1 to 3 carbon atoms or trifluoromethyl; 4-carboxamido-5-imidazolyl; 3-pyrazolyl; 5-methyl-3-isoxazolyl or 5-tetrazolyl; or $R^2$ and $R^3$ together with the nitrogen atom form a morpholine, proline, pyrrolidine, methylpiperazine or imidazole ring.

2. A compound as claimed in claim 1 in which $R^2$ represents hydrogen, a straight or branched alkyl group having 1 to 3 carbon atoms, and $R^3$ represents a cyclohexyl group.

3. A compound as claimed in claim 1 in which $R^1$ represents a straight or branched alkyl group having 1 to 4 carbon atoms, $R^2$ represents hydrogen, and $R^3$ represents tetrahydrothiophen-2-on-3-yl.

4. A compound as claimed in claim 1 in which $R^1$ represents a straight or branched alkyl group having 1 to 4 carbon atoms, $R^2$ represents hydrogen, and $R^3$ represents 2-thiazolyl or 2-thiazolyl substituted by a $C_1$–$C_3$ lower alkyl at the 4 and/or 5 positions of the ring.

5. A compound as claimed in claim 1 in which $R^1$ represents a straight or branched alkyl group having 1 to 4 carbon atoms, $R^2$ represents hydrogen, and $R^3$ represents 2-thiazolin-2-yl.

6. A compound as claimed in claim 1 in which $R^1$ represents a straight or branched alkyl group having 1 to 4 carbon atoms, $R^2$ represents hydrogen, and $R^3$ represents 2-benzothiazolyl.

7. A compound as claimed in claim 1 in which $R^1$ represents a straight or branched alkyl group having 1 to 4 carbon atoms, R2 represents hydrogen, and $R^3$ represents 2-pyrimidyl.

8. A compound as claimed in claim 1 in which $R^1$ represents a straight or branched alkyl group having. 1 to 4 carbon atoms, $R^2$ represents hydrogen, and $R^3$ represents 2-hydroxy-4-pyrimidyl.

9. A compound as claimed in claim 1 in which $R^1$ represents a straight or branched alkyl group having 1 to 4 carbon atoms, $R^2$ represents hydrogen, and $R^3$ represents 2-thienyl.

10. A compound as claimed in claim 1 in which $R^1$ represents a straight or branched alkyl group having 1 to 4 carbon atoms, $R^2$ represents hydrogen, and $R^3$ represents 1, 3, 4-thiadiazol-2-yl or 1, 3, 4-thiadiazol-2-yl substituted by a Cl-C3 lower alkyl or trifluoromethyl group.

11. A compound as claimed in claim 1 in which $R^1$ represents a straight or branched alkyl group having 1 to 4 carbon atoms, $R^2$ represents hydrogen, and R3 represents 4-carboxamido-5-imidazolyl.

12. A compound as claimed in claim 1 in which $R^1$ represents a straight or branched alkyl group having 1 to 4 carbon atoms, $R^2$ represents hydrogen, and $R^3$ represents 3-pyrazolyl.

13. A compound as claimed in claim 1 in which $R^1$ represents a straight or branched alkyl group having 1 to 4 carbon atoms, $R^2$ represents hydrogen, and $R^3$ represents 5-methyl-3-isoxazolyl.

14. A compound as claimed in claim 1 in which $R^1$ represents a straight or branched alkyl group having 1 to 4 carbon atoms, $R^2$ represents hydrogen, and $R^3$ represents 5-tetrazolyl.

15. A pharmaceutical composition comprising a pharmaceutically effective amount of a compound as claimed in claim 1 in association with a pharmaceutically acceptable carrier or diluent.

16. A composition as claimed in claim 15 in a form suitable for oral or parenteral administration.

17. A composition as claimed in claim 16 in oral form as a tablet.

18. A composition as claimed in claim 17 in the form of a slow release tablet.

19. A composition as claimed in claim 18 containing 10 to 200 mg of active ingredient per tablet.

* * * * *

UNITED STATES PATENT AND TRADEMARK OFFICE
CERTIFICATE OF CORRECTION

PATENT NO. : 5,158,950
DATED : October 27, 1992
INVENTOR(S) : Choong S. Kim et al It is certified that error appears in the above-indentified patent and that said Letters Patent is hereby corrected as shown below:

Claim 1, Column 27, Line 49, change "substituented" to --substituted--;

Claim 1, Column 27, Line 54, change "s" to --substituted by a lower--;

Claim 7, Column 28, Line 19, change "R2" to --$R_2$--;

Claim 8, Column 28, Line 22 after "having" delete --.--;

Claim 10, Column 28, Line 34, change "C1-C3" to --$C_1$-$C_3$--; and

Claim 11, Column 28, Line 38, change "R3" to --$R_3$--.

Signed and Sealed this

First Day of February, 1994

Attest:

BRUCE LEHMAN

Attesting Officer     *Commissioner of Patents and Trademarks*